US007279129B2

(12) United States Patent
Lanz et al.

(10) Patent No.: US 7,279,129 B2
(45) Date of Patent: Oct. 9, 2007

(54) METHOD AND APPARATUS FOR CONTROL OF CHEMICAL OR BIOLOGICAL WARFARE AGENTS

(75) Inventors: Bret E. Lanz, Manhattan, KS (US); Thomas Allen, Manhattan, KS (US)

(73) Assignee: NanoScale Corporation, Manhattan, KS (US)

( * ) Notice: Subject to any disclaimer, the term of this patent is extended or adjusted under 35 U.S.C. 154(b) by 576 days.

(21) Appl. No.: 10/452,650

(22) Filed: Jun. 2, 2003

(65) Prior Publication Data

US 2005/0158207 A1 Jul. 21, 2005

Related U.S. Application Data

(63) Continuation-in-part of application No. 10/146,376, filed on May 14, 2002, now abandoned.

(51) Int. Cl.
*A61L 2/238* (2006.01)

(52) U.S. Cl. ........................................ 422/28; 422/292

(58) Field of Classification Search ..................... None
See application file for complete search history.

(56) References Cited

U.S. PATENT DOCUMENTS 3,998,363 A * 12/1976 Beres et al. ............ 222/321.9
4,659,560 A * 4/1987 Bews et al. .................. 424/47
5,403,587 A * 4/1995 McCue et al. ............. 424/736
5,463,167 A 10/1995 Ou
5,547,649 A 8/1996 Beck et al.
5,648,591 A 7/1997 Donecker et al.
5,712,219 A 1/1998 Klabunde et al.
5,759,939 A 6/1998 Klabunde et al.
5,914,436 A 6/1999 Klabunde et al.
5,939,146 A 8/1999 Lavernia
5,990,373 A 11/1999 Klabunde
6,025,034 A 2/2000 Strutt et al.
6,045,925 A 4/2000 Klabunde et al.
6,057,488 A 5/2000 Koper et al.
6,087,294 A 7/2000 Klabunde et al.
6,093,236 A 7/2000 Klabunde et al.
6,235,351 B1 5/2001 DiMarzio et al.
6,258,417 B1 7/2001 Goswami et al.
6,264,922 B1 7/2001 Wood et al.
6,276,287 B1 8/2001 Imai et al.
6,417,423 B1 7/2002 Koper et al.

(Continued)

FOREIGN PATENT DOCUMENTS

JP 2001-161854 A * 6/2001

*Primary Examiner*—E. Leigh McKane
(74) *Attorney, Agent, or Firm*—Hovey Williams LLP

(57) ABSTRACT

Metal oxide area decontamination apparatus (10) is provided which is designed for rapid, emergency situation decontamination of areas contaminated with potentially harmful or lethal chemical and/or biological warfare agents or other hazardous substances. The apparatus (10) preferably includes a pressurizable metallic container (12) equipped with a valve-type delivery nozzle assembly (16), so that upon a manipulation of the assembly (16), a spray of metal oxide and/or metal hydroxide particles is generated; the particles are selected and sized in order to destroy or chemisorb the contaminating agents. The preferred decontamination agent is MgO aggregated to an average aggregate size of from about 50 nm-10 microns. The particles are mixed with a gaseous or liquid propellant within the container (12) allowing rapid and thorough particle cleanout when the nozzle assembly (16) is actuated.

11 Claims, 6 Drawing Sheets

U.S. PATENT DOCUMENTS

2002/0028288 A1  3/2002  Rohrbaugh et al.
2002/0035032 A1  3/2002  Koper et al.
2002/0037256 A1  3/2002  Nocerino et al.
2002/0045010 A1  4/2002  Rohrbaugh et al.

* cited by examiner

METHOD AND APPARATUS FOR CONTROL OF CHEMICAL OR BIOLOGICAL WARFARE AGENTS

RELATED APPLICATION

This application is a continuation-in-part of U.S. patent application Ser. No. 10/146,376, filed May 14, 2002, now abandoned which is incorporated by reference herein.

BACKGROUND OF THE INVENTION

1. Field of the Invention

The present invention is broadly concerned with apparatus and methods for area decontamination and is of particular utility for emergency situations where a given area must be at least partially and rapidly decontaminated. More particularly, the invention is concerned with such devices and methods which include a container that is or can be pressurized containing sprayable mixture therein including reactive metal oxide and/or metal hydroxide particles (e.g., MgO) and having a selectively operable spray nozzle assembly coupled with the container. The invention finds particular utility for destroying or chemisorbing a variety of chemical, biological and/or hazardous agents, especially chemical/biological warfare agents.

2. Description of the Prior Art

Governments around the world have become increasingly concerned about the effects of chemical and/or biological warfare agents and other types of hazardous substances, particularly in light of the recent rise in terrorism. The potentially catastrophic results which could ensue in high density population centers subjected to such agents are well known to disaster experts. While a number of proposals have been adopted for dealing with warfare agents and similar substances, in general these deal with massive decontamination or cleanup efforts. However, it is contemplated that, in many instances, there will be a need for immediate, at least partial decontamination over restricted areas in order to minimize the risk to affected populations.

There are currently two general types of decontamination methods for biological agents, namely chemical disinfection and physical decontamination. Chemical disinfectants such as hypochlorite solutions are useful but are corrosive to most metals and fabrics, and to human skin. Liquid-like foam disinfectants have also been used, and generally require water and pressurized gases for efficient application. Physical decontamination usually involves dry heat up to 160° C. for 2 hours or steam or super-heated steam for about 20 minutes. Sometimes UV light can be used effectively, but it is difficult to implement in actual practice. Techniques used for decontamination of areas subjected to chemical warfare agents are more varied, and depend principally upon the nature of the agent in question.

U.S. Pat. No. 5,914,436 describes methods for the destruction of unwanted compounds such as chlorocarbons, chlorofluorocarbons and PCBs, making use of metal oxide composites as adsorbents. Also, U.S. Pat. No. 6,057,488 describes the use of metal oxide nanoparticles for the destructive adsorption of biological and chemical contaminants, including biological and chemical warfare agents. However, these references do not describe techniques for the rapid use of metal oxides in emergency-type situations.

It is known that magnesium oxide and other similar oxides can be produced by varying techniques. In the case of MgO, very fine nanometer sized particles are best produced using aerogel preparation methods (and thus is often referred to "AP—MgO") such as those described by Utamapanya et al., *Chem. Mater.*, 3:175-181 (1991). A specific example of AP—MgO preparation is set forth in Example 1 of the aforementioned U.S. Pat. No. 6,057,488. MgO particles can also be prepared by conventional methods (and is hence often referred to as "CP—MgO"), involving boiling commercially available MgO followed by microwave drying thereof and dehydration under vacuum at high temperature, e.g., 500° C.

SUMMARY OF THE INVENTION

The present invention overcomes the problems outlined above and provides improved apparatus and methods for area decontamination making use of metal oxide and/or metal hydroxide particles. Broadly speaking, a preferred decontamination apparatus includes a container with a pressurized, sprayable mixture within the container including metal oxide and/or metal hydroxide particles and mixtures thereof, and a propellant. A spray nozzle is coupled with the container and is selectively operable for generating a spray of the metal particles from the nozzle. In an emergency situation, a worker can actuate the spray nozzle to create a spray or fog of the particles, which are effective for destroying or chemisorbing (usually via an adsorption mechanism) a variety of undesirable substances such as chemical and/or biological warfare agents.

Another preferred apparatus includes a container with a pressurizable, sprayable mixture within the container including metal oxide and/or metal hydroxide particles and mixtures thereof. A spray nozzle presenting an outlet is coupled with the container and selectively operable for generating a spray of the metal particles from the nozzle outlet. The apparatus further includes means for creating a pressure gradient between the container and the nozzle outlet enabling the mixture to flow from the container toward the nozzle, thereby eliminating the need for the addition of a propellant to the mixture. In preferred forms, this pressure gradient creating means will comprise a pump which will increase the pressure of the fluids within the container, however, the pump may also be operable to decrease the pressure at the nozzle outlet. Such pumps include both mechanical and manually operable positive displacement pumps commonly known to those skilled in the art. Exemplary pumps are those found on pump sprayers and hand pump spray bottles.

Preferably, the metal oxide and/or metal hydroxide is selected from the group consisting of alkali metal, alkaline earth metal, transition metal, actinide and lanthanide oxides and/or hydroxides, and mixtures thereof. The metal oxides may be coated and/or modified to improve their utility. A preferred oxide is MgO. The MgO may be prepared by any one of the known techniques, so long as the ultimate size of the MgO is efficient for spraying and cleanout of the oxide from the container. That is, if the effective size of the oxide is too small, it may have a tendency to cake within the container and not be dispersed; on the other hand, if the oxide effective size is too large, it may be difficult to disperse the oxide over a wide area through use of the internal propellant. Therefore, an optimum effective size must be determined for the oxide(s) employed. In the case of the preferred MgO, it has been found that the oxide nanocrystals should be aggregated so that the average aggregate size is from about 50 nm-10 microns.

It is within the scope of the present invention for the metal oxide composition to comprise a mixture of nanocrystalline MgO and $TiO_2$ particles. The weight ratio of MgO to $TiO_2$ is between about 99:1 to 1:99, more preferably between about 80:20 to 20:80, and most preferably between about 70:30 to 30:70. As with the MgO particles noted above, the MgO and $TiO_2$ particles may be aggregated so as to optimize spraying efficiency thereby giving an average aggregate size from about 50 nm-10 microns.

Almost any suitable liquid or gaseous propellant can be used in the decontamination apparatus, such as nitrogen, the noble gases, carbon dioxide, air or volatile hydrocarbon or fluorocarbon compounds. Pressures within the apparatus or that are applied are normally within the range of from about 5-600 psi.

It is also within the scope of the invention for the metal oxide and/or metal hydroxide particles to be manually applied to a particular area for at least partial decontamination thereof. During manual application, the particles are preferably in the form of a finely divided powder which is contacted with the undesirable agent or substance. The particles are sprinkled, dusted or otherwise dispersed on the area to be decontaminated. Preferably, the particles comprise a mixture of nanocrystalline MgO and $TiO_2$ particles as described above.

DETAILED DESCRIPTION OF THE PREFERRED EMBODIMENTS

Figure 6:
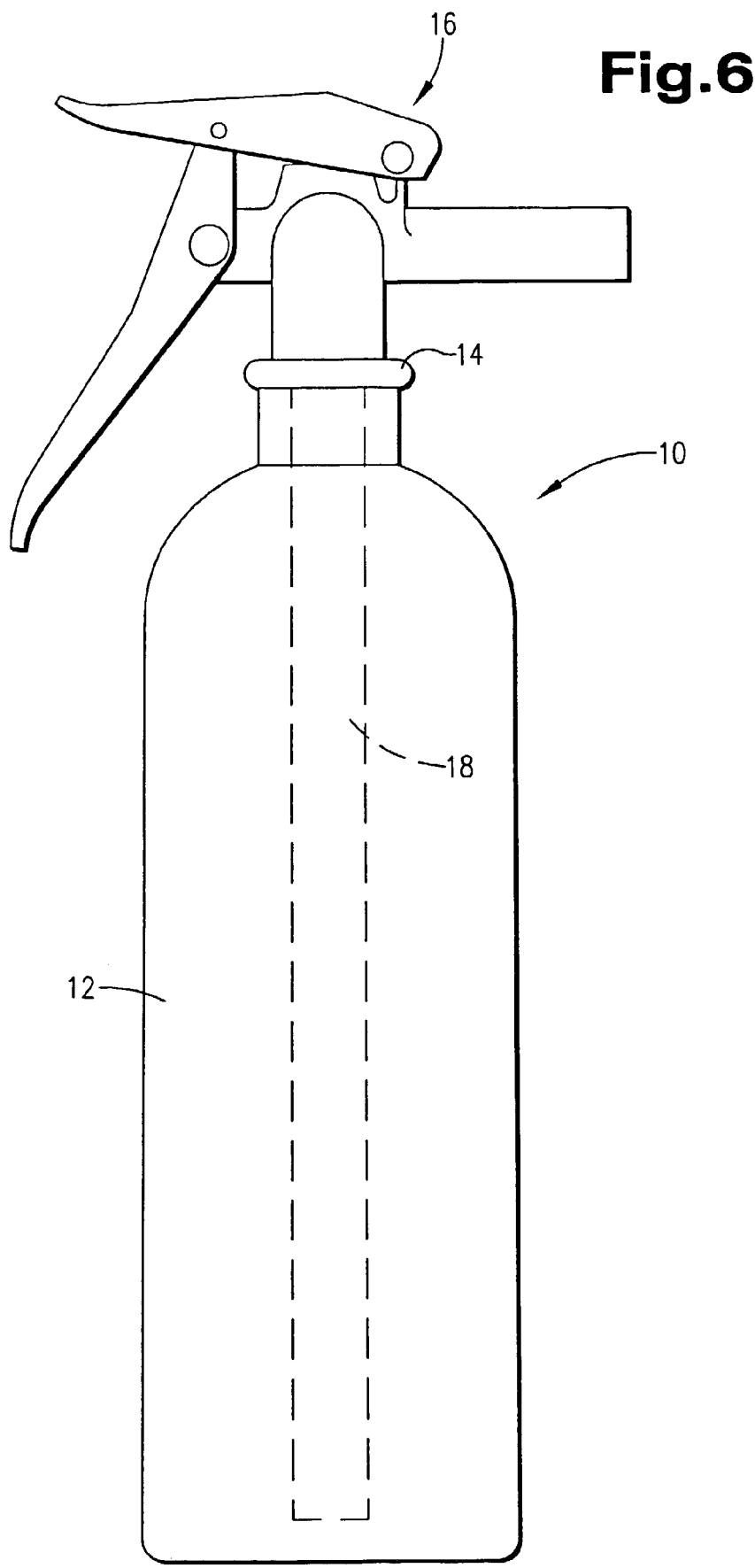
FIG. 6 is an elevational view of a pressurized fire extinguisher-type container useful in carrying out the invention, with the container siphon illustrated in phantom.

In a general aspect, the present invention is directed to pressurized or pressurizable delivery systems and mixtures for the spraying and application of reactive metal oxide and/or metal hydroxide particles in order to destroy or chemisorb a variety of chemical and biological warfare agents. One implementation of the invention is depicted in FIG. 6 in the form of a pressurized device 10. In this instance, the device 10 is a typical fire extinguisher-type unit including a thick-walled metal bottle or container 12 having an outlet neck 14. A conventional manually operated valve assembly 16 is fitted into neck 14 as shown. The valve assembly also includes a siphon tube 18 extending downwardly within the confines of container 12. However, it will be appreciated that the invention is in no way limited to any specific type of container; broadly speaking, so long as a given container can be pressurized to the desired level and is equipped with a valve or similar mechanism for selectively emitting or spraying the particles therein, it will suffice.

The apparatus of FIG. 6 may be modified by replacing valve assembly 16 with a pump spraying assembly (not shown). The pump spraying assembly is operable to create a pressure gradient across outlet neck 14 by either increasing the pressure within container 12, or decreasing the pressure (i.e., create a vacuum) within siphon tube 18. Either way, the pressure within container 12 will be greater than that within siphon tube 18 thereby enabling the contents of the container 12 to flow across outlet neck 14 via siphon tube 18 and out of container 12.

In one exemplary embodiment, area decontamination devices were prepared using fire extinguisher bottles having a 3-inch diameter, commonly sold as "2½ pound" units. In this case the decontamination agent was conventionally prepared MgO, having a particle size in which 95% of the particles had a diameter of less than 2 microns, and with a surface area (BET) of about 250-300 $m^2/g$. The devices contained a propellant made up of a mixture of $N_2$ and He. The bottles were pressurized with the propellant to a level of about 195-200 psi. These devices were equipped with an adjustable nozzle with a 0.128-inch outlet, so that a "jet-stream" of powder was generated when the nozzle was actuated.

Larger decontamination devices can be similarly produced using "5 pound" fire extinguisher units having a diameter of 4¾-inches. In such instances, it may be useful to add a lubricant to assist in cleanout times and percentages; in practice, 200 mesh Muscovite mica can be used at a level of from about 5-10% by weight, based upon the total weight of the MgO taken as 100% by weight.

The invention is useful against a wide variety of chemical, biological and/or hazardous agents, of the type described in Marrs, T. C., et al.; *Chemical Warfare Agents, Toxicology and Treatment*; John Wiley & Sons: Chichester, England, 1996; and/or Compton, J. A. F.; *Military Chemical and Biological Agents, Chemical and Toxicological Properties*; The Telford Press: Caldwell, N.J.; 1988; and/or Somani, S. M.; *Chemical Warfare Agents*; Academic Press: San Diego, 1992 (all of the foregoing are incorporated by reference herein). Other target materials are described in U.S. Pat. No. 5,990,373 and specifically include $C_6H_3(OH)(NO_2)_3$, $C_6H_5(Br)(CN)$, $C_6H_5CH_2CN$, $(CF_3)_2C=CF_2$, HCN, $P(O)(OCH_2CH_3)(CN)(N(CH_3)_2)$, ClCN, $Zn(CH_2CH_3)_2$, $Hg(CH_3)_2$, $Fe(CO)_5$, $[(CH_3)_2CHO]P(O)(CH_3)(F)$, $S(CH_2CH_2CH_2Cl)_2$, $C_6H_5C(O)CH_2C-1$, $C(O)Cl_2$, and $C_6Cl_5OH$. U.S. Pat. No. 6,057,488 describes applicable biological agents such as those selected from the group consisting of *Bacillus cereus, Bacillus globigii, Chlamydia*, and *Rickettsiae*. U.S. Pat. No. 5,914,316 describes still further applicable target substances such as chlorocarbons, chlorofluorocarbons, and heteroatom compounds having an atom selected from the group consisting of N, P or S or a halogen atom. As indicated previously, a principal utility foreseen for the invention is the destruction or chemisorption of chemical and biological warfare agents. The following table also sets forth a number of nerve and blister agents, as well as common biological warfare agents, which can be treated to good effect in accordance with the invention.

| Military Designation Organophosphate | Common Name(s) | Proper Name, Chemical Formula |
|---|---|---|
| Nerve Agents | | |
| GA | Tabun | Ethyl N-dimethylphosphoramidocyanidate, $CH_3CH_2OP(O)(CN)N(CH_3)_2$ |
| GB | Sarin | Isopropyl methylphosphonofluoridate, $CH_3P(O)(F)OCH(CH_3)_2$ |
| GD | Soman | Pinacolyl methylphosphonofluoridate, $CH_3P(O)(F)OCH(CH_3)C(CH_3)_3$ |
| GE | — | Isopropyl ethylphosphonofluoridate, $CH_3CH_2P(O)(F)OCH(CH_3)_2$ |
| GF | — | Cyclohexyl methylphosphonofluoridate, $CH_3P(O)(F)OCHC_5H_{10}$ |
| VX | — | O-Ethyl-S-[2(diisopropylamino)ethyl methylphosphonothioate, $(CH_3CH_2O)(CH_3)(O)PSCH_2CH_2N[CH(CH_3)_2]_2$ |
| VE | — | O-Ethyl-S-[2(diethylamino)ethyl ethylphosphonothioate, $(CH_3CH_2O)(CH_3CH_2)(O)PSCH_2CH_2N(CH_2CH_3)$ |
| Mustard Agents | | |
| HD | Mustard | Bis 2-chloroethyl ethyl sulfide, $ClCH_2CH_2SCH_2CH_2Cl$ |
| $HN_1$ | Nitrogen Mustard 1 | N-ethyl-2,2'-di(chloroethyl)amine, $CH_3CH_2N(CH_2CH_2Cl)_2$ |
| $HN_2$ | Nitrogen Mustard 2 | N-methyl-2,2'-di(chloroethyl)amine, $H_3CN(CH_2CH_2Cl)_2$ |
| $HN_3$ | Nitrogen Mustard 3 | 2,2'2''-tri(chloroethyl)amine, $N(CH_2CH_2Cl)_3$ |

| Common Name | Proper Name | Class |
|---|---|---|
| Anthrax | *Bacillus anthracis* | Bacterial, bacillus |
| Cholera | *Vibrio cholera* (multiple subtypes) | Bacterial |
| Plague, Bubonic Plague, Black Death | *Yersinia pestis* | Bacterial, bacillus |
| Q Fever | *Coxiella burnetti* | Rickettsia |
| Dengue Fever, Breakbone Fever | Dengue Fever | Viral, hemorrhagic |
| Flu, Grippe | Influenza (multiple subtypes) | Viral |
| Small pox | Small pox | Viral |
| Yellow Fever | Yellow Fever | Viral, hemorrhagic |

The solid active particles useful in the invention include one or more metal oxides and/or metal hydroxides, and may be aerogel or conventionally prepared nanoparticles, or larger particles which are commercially available. The metal oxides or metal hydroxides are preferably selected from the group consisting of alkali metal, alkaline earth metal, transition metal, actinide and lanthanide oxides and hydroxides, and mixtures thereof. Particularly preferred metal oxides are selected from the group consisting of MgO, CaO, ZnO, $Al_2O_3$, $TiO_2$, and $SnO_2$ and mixtures thereof. For reasons of cost and ease of use, MgO is especially preferred.

In another preferred embodiment, the solid active particles used with the invention are a mixture of MgO and $TiO_2$. In this embodiment, the weight ratio of MgO to $TiO_2$ is between about 99:1 to 1:99, more preferably 80:20 to 20:80, and most preferably 70:30 to 30:70. An example of a preferred MgO/$TiO_2$ mixture according to the invention comprises 65% by weight MgO and 35% byweight $TiO_2$. The MgO/$TiO_2$ mixture maybe substituted for the MgO mixture in the area decontamination devices described above and illustrated in FIG. 6.

The metal particles should have a non-aggregated particle size of from about 2-20 nm, more preferably from about 4-10 nm, and surface areas (BET) of from about 200-700 $m^2/g$ and more preferably from about 225-275 $m^2/g$ for CP MgO and 550-650 $m^2g$ for AP MgO. However, in order to insure the most rapid application of metal oxide from a pressurized container, consistent with substantial cleanout of the container, the particles should be aggregated so that the average aggregate size should be from about 50 nm-10 microns, more preferably from about 500 nm-2 microns. Such aggregate sizes have been shown to give superior application results, as compared with smaller nanoscale-sized particles or crystallites.

It is also possible to use in the context of the invention composite products containing one or more metal oxides or coated by resins, polymers, waxes, oils, etc. For example, U.S. Pat. No. 5,914,436 describes finely divided composite materials made up of a first metal oxide support which are at least partially coated with a quantity of a second metal oxide different from the first metal oxide and selected from the group consisting of the transition metal oxides. Particularly preferred transition metal oxides include the oxides of titanium, vanadium, chromium, manganese, iron, copper, nickel and cobalt, such as $TiO_2$, $V_2O_5$, $Cr_2O_3$, $Mn_2O_3$, $Fe_2O_3$, $Cu_2O$, CuO, NiO, CoO and mixtures thereof.

In preferred forms, the first metal oxide is advantageously selected from the group consisting of MgO and CaO, whereas the second oxide is preferably $Fe_2O_3$, $TiO_2$, $V_2O_3$ and $Mn_2O_3$. The particles of the first metal oxide should be single crystallites or polycrystallite nanoscale aggregations and should have an average crystallite size of up to about 20 nm, and more preferably from about 4-10 nm; the second metal oxide should be in the form of an extremely thin layer or coating applied onto the surface of the first metal oxide, giving an average overall size for the composite of up to about 21 nm, and more preferably from about 5-11 nm. The bulk composites of the invention should have an average surface area of at least about 15 m$^2$/g, and more preferably from about 30-600 m$^2$/g. More preferred ranges are from about 100-600 m$^2$/g and most preferably from about 250-600 m$^2$/g.

Generally, the first metal oxide should be present in substantial excess relative to the second oxide. Thus, the first metal oxide comprises from about 60-99% by weight of the total composite material, and more preferably from about 75-99% by weight, and most preferably from about 95-99% by weight. Correspondingly, the second metal oxide should comprise from about 1-40% by weight of the total composite, and more preferably from about 1-25% by weight, and most preferably from about 1-5% by weight. The coverage of the first oxide by the second oxide should be quite extensive, e.g., at least about 75% of the surface area of the first metal oxide particles should be covered with the second oxide, and more preferably from about 90-100% of this surface area should be covered.

Furthermore, as noted above, it is possible to use in the context of the invention composite products coated by resins, polymers, waxes, oils, etc. These composites comprise a metal oxide support coated with one of the latter materials. Preferably, the coating should be in the form of thin layer similar to the layer formed by the second metal oxide discussed above. Similarly, the composite particle should comprise the resin, polymer, wax, or oil coating within the same weight ranges as the second metal oxide described above.

When the above-described composites are employed, the aggregated average particle size should be from about 50 nm-10 microns, more preferably from about 500 nm-2 microns.

A variety of conventional propellants can be used in the context of the invention. As noted above, N$_2$ is often preferred for reasons of cost and availability; however, virtually any other pressurizable aqueous or non-aqueous liquid or gaeous propellant material could be used, e.g., such as other inert or noble gases, e.g., He, Ar, Kr, Xe, Rn and mixtures thereof), carbon dioxide, air, or hydrocarbon gases. Often, a suspending medium is also used with the propellant, with exemplary suspension media being the hydrocarbons, fluorinated hydrocarbons, hydrofluoroethers such as the HFE family of compounds available from 3M under the names HFE-7100, 7200, and 7500 (a commercial mixture of methyl fluoro isobutyl ether and methyl nonafluorobutyl ether) another high vapor pressure, low-boiling point media. The pressure levels within the decontamination devices of the invention are likewise variable, depending upon intended uses. Generally speaking, these pressure levels should be from about 5-600 psi, more preferably from about 175-225 psi.

The following examples set forth a series of tests to determine the efficacy of metal oxide particles in the destruction or chemisorption of chemical warfare agents. It is to be understood, however, that these examples are provided by way of illustration and nothing therein should be taken as a limitation upon the overall scope of the invention.

EXAMPLE 1

In this example, the relative effectiveness of various magnesium oxide powders were tested, versus commercially available activated carbon. In particular, laboratory-prepared AP—MgO, pilot plant prepared AP—MgO, CP—MgO and commercially available MgO were all tested versus Ambersorb activated carbon. In each test, a mustard gas chemical warfare simulant (CWS), 2-chloroethyl ethyl sulfide (2-CEES) was loaded at 25% relative to a reactive nanoparticle (RNP) sample (CWS/RNP×100) onto approximately 0.15 g of RNP in a conical bottom, 4-dram vortex mixing vial. In certain cases, the reaction mixture was scaled down when the RNP was available in limited quantities; however, the loading was held constant regardless of scale. Each mixture was capped and vortex mixed using a magnetic stirring plate for about 20 seconds. The destruction/chemisorption reaction was carried out at room temperature and atmospheric pressure for 120 minutes. After this time, an extractive solvent (10 ml of n-hexane) was added to each vial, followed by sonication for 20 minutes. Thereafter, each sample was centrifuged for 5 minutes to separate the phases. A 5 ml aliquot of the solvent was then taken, and 5 µl of internal standard (n-decane) was added. The reaction products were then characterized using quantitative GC/MS.

Figure 1:
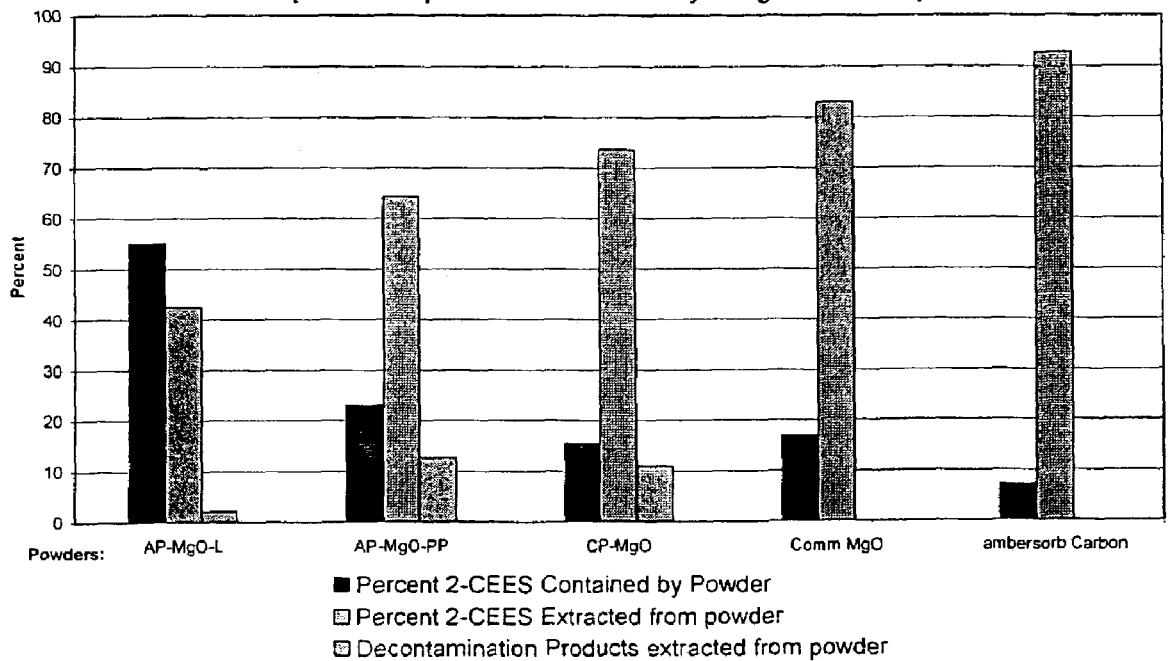
FIG. 1 is a bar graph illustrating the results of the comparative tests described in Example 1.

The results of this test are graphically set forth in FIG. 1. In this graph, the lefthand bars represent the percent 2-CEES retained by the powder, the next bar to the right represents the percent 2-CEES extracted from the powder, and the righthand bar (where present) represents the decontamination products extracted from the powder.

As can be seen from FIG. 1, all of the MgO products were superior to the activated carbon in terms of percent 2-CEES retained by the powder. Furthermore, all of the MgO products were better in terms of the percent 2-CEES extracted from the powder. Finally, the pilot plant AP—MgO and CP—MgO gave the best results in terms of decontamination products extracted from the product.

EXAMPLE 2

In this example, the effectiveness of CP-MgO having a specific surface area (BET) of 275 m$^2$/g was tested against an available ion exchange resin standard used by the military (Ambergard XE-555 (M291), specific surface area 131 m$^2$/g). In this test, another CWS, paraoxon, was used. In each test, 9 µl of paraoxon was added to a round bottom flask containing 200 ml of pentane. This solution was stirred and then pumped to a flow-through cuvette, where a UV-VIS spectrum of the reference was obtained at 266 nm. Once the baseline was established, 0.2 g of the test powder was added to the stirring solution and another UV-VIS spectrum (266 nm) was collected at 1 minute intervals up to 10 minutes, and then at 5 minute intervals for a total period of 1 hour.

Figure 2:
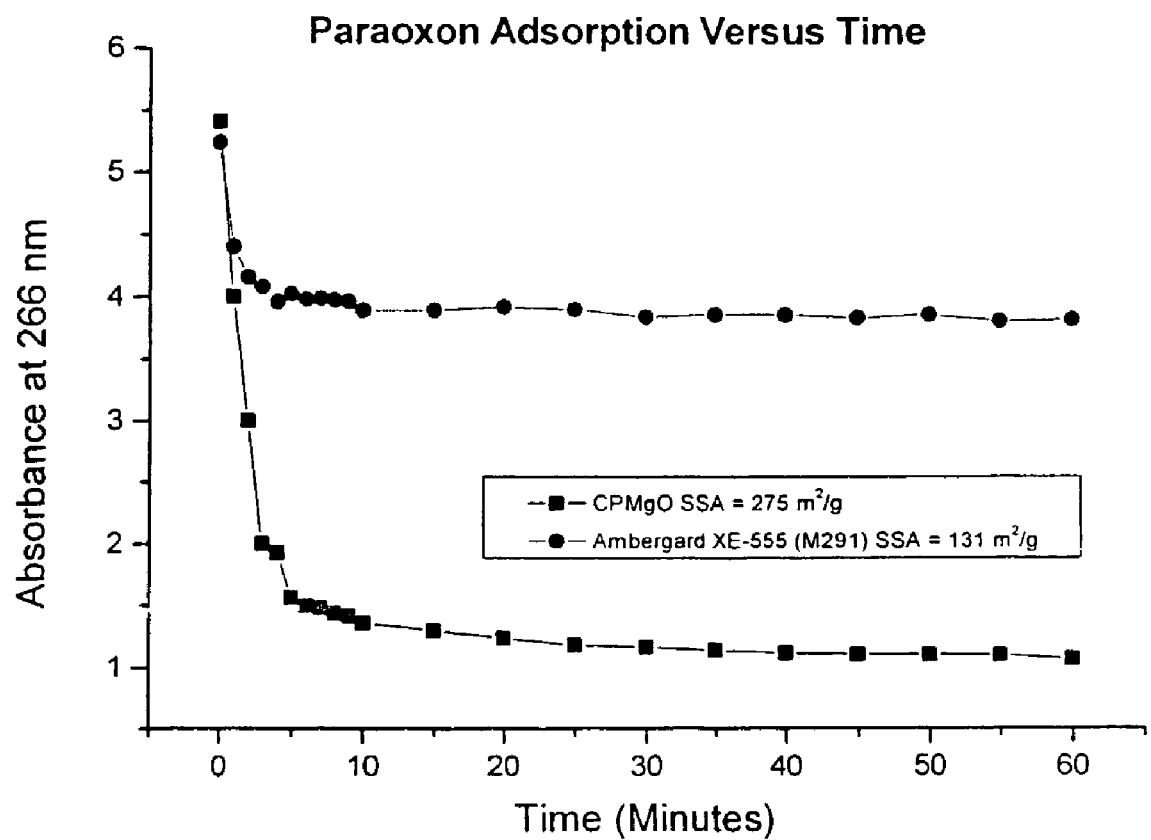
FIG. 2 is a graph illustrating the results of the comparative tests described in Example 2.

FIG. 2 sets forth the results of this test, and clearly demonstrates that the CP—MgO was superior, i.e., the lower absorbance confirming that the CWS reacted with the CP—MgO to a greater extent than the ion exchange resin.

EXAMPLE 3

In this example, the destruction/chemisorption of 2-CEES was measured using Headspace GC. The experiment was conducted using an HP5890 gas chromatograph equipped with a Tekmar 7000 Headspace Autosampler. Headspace vials were loaded with 0.1 g of the test samples (CP—MgO and Ambergard XE555 (M291)) and 23.3 µl 2-CEES. The destruction/chemisorption reaction was allowed to proceed for 2 hours. The volatile reactant and decomposition products present in the Headspace were analyzed by GC equipped with a flame ionization detector (FID).

Figure 3:
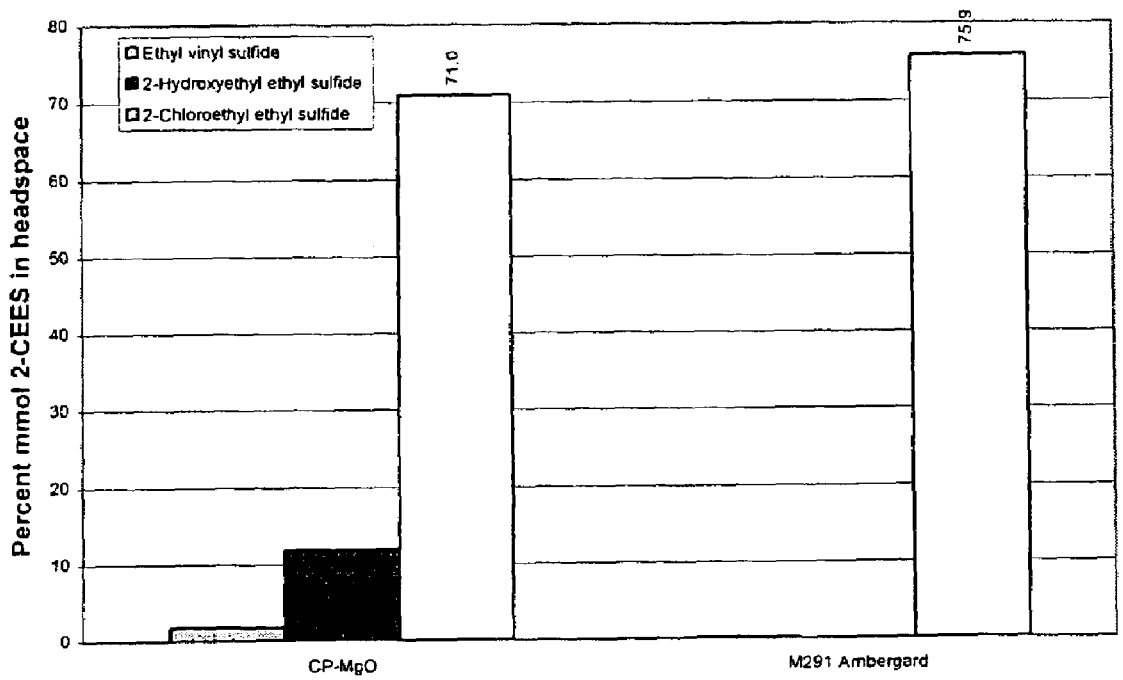
FIG. 3 is a bar graph illustrating the results of the comparative tests described in Example 3.

FIG. 3 sets forth the results of this test, where the leftmost part represents ethyl vinyl sulfide, the middle bar represents 2-hydroxyethyl ethyl sulfide (a decomposition product) and the large bars represent 2-CEES. As illustrated, the CP—MgO analysis demonstrated the presence of decomposition products, whereas the ion exchange resin failed to decompose any of the 2-CEES.

EXAMPLE 4

In this example, the effectiveness of CP—MgO having a specific surface area (BET) of 275 $m^2/g$ was tested against the ion exchange resin standard used in Example 2. In this test, another CWS, diethyl phenylthiomethylphosphonate (DEPTMP) was used. In each test, neat DEPTMP (22 μl) was added to a stirred round bottom flask containing 200 ml pentane. This solution was stirred and then pumped to a flow-through cuvette, where a UV-VIS spectrum of the reference was obtained at 255 nm using a Varian Cary 100 Bio UV-VIS spectrophotometer. Once the baseline was established, 0.2 g of the test powder was added to the stirring solution and another UV-VIS spectrum (266 nm) was collected at 1 minute intervals up to 10 minutes, and then at 5 minute intervals for a total period of 1 hour. The destruction/chemisorption of DEPTMP by the test sample was assessed by the loss of characteristic DEPTMP adsorption at 255 nm.

Figure 4:
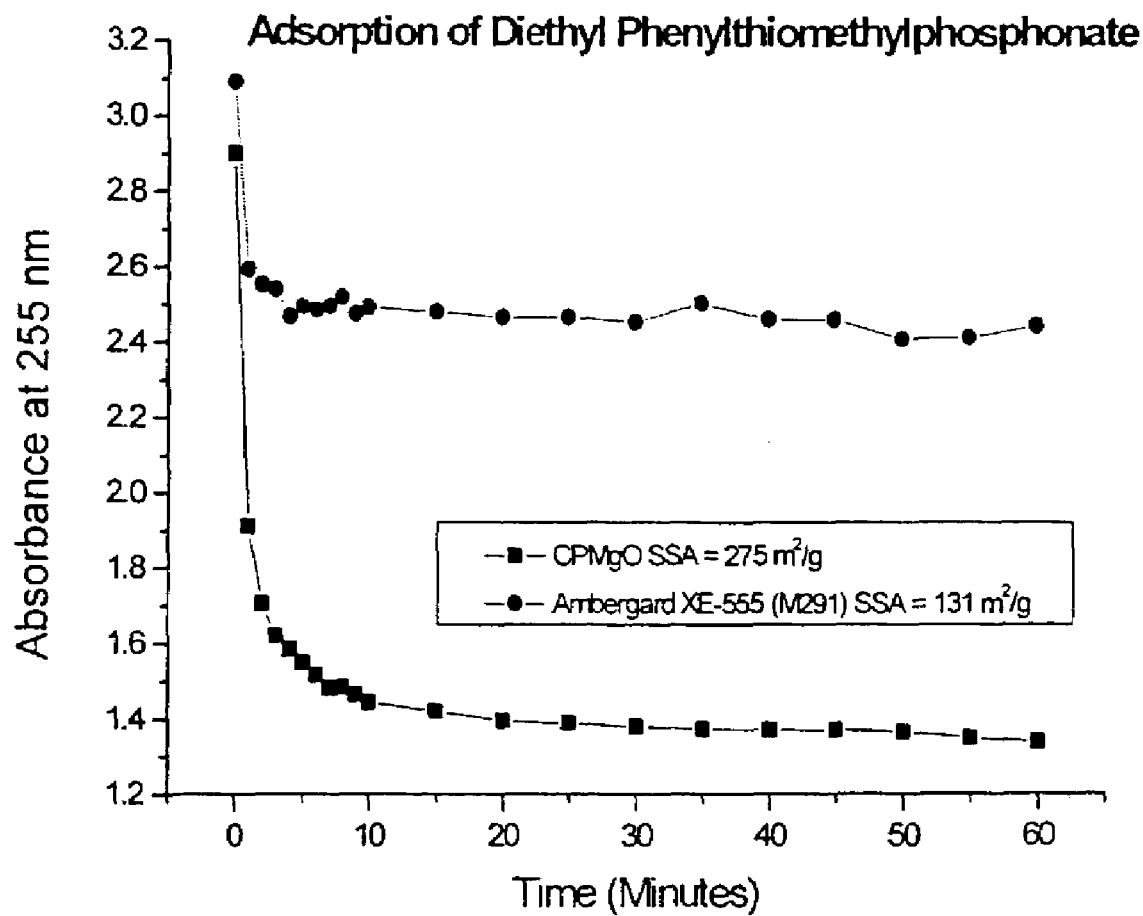
FIG. 4 is a graph illustrating the results of the comparative tests described in Example 4.

FIG. 4 sets forth the results of this test, and clearly demonstrates that the CP—MgO was superior, i.e., the lower adsorbance confirming that the CWS reacted with the CP—MgO to a much greater extent than the ion exchange resin.

EXAMPLE 5

In this test, the destruction/chemisorption of 2-CEES was determined by FT-IR, using a Nicolet Protégé 460 FT-IR spectrophotometer. Each sample powder (CP—MgO having a specific surface area of 275 $m^2/g$ and Ambergard XE-555 (M291), specific surface area 131 $m^2/g$, 0.1 g) was added to a reaction flask-of a special gas phase infrared cell. The cell was then evacuated to the $10^{-3}$ torr on a vacuum line and placed into the FT-IR. A background spectrum was obtained, and then 2-CEES (12 μl) was injected into the reaction flask of the cell through a side port. The vapor phase of the sample was monitored as a function of time for up to 5 hours. Dehydrochlorination of the 2-CEES was observed by the formation of the vinyl peak at 1585 $cm^{-1}$.

Figure 5:
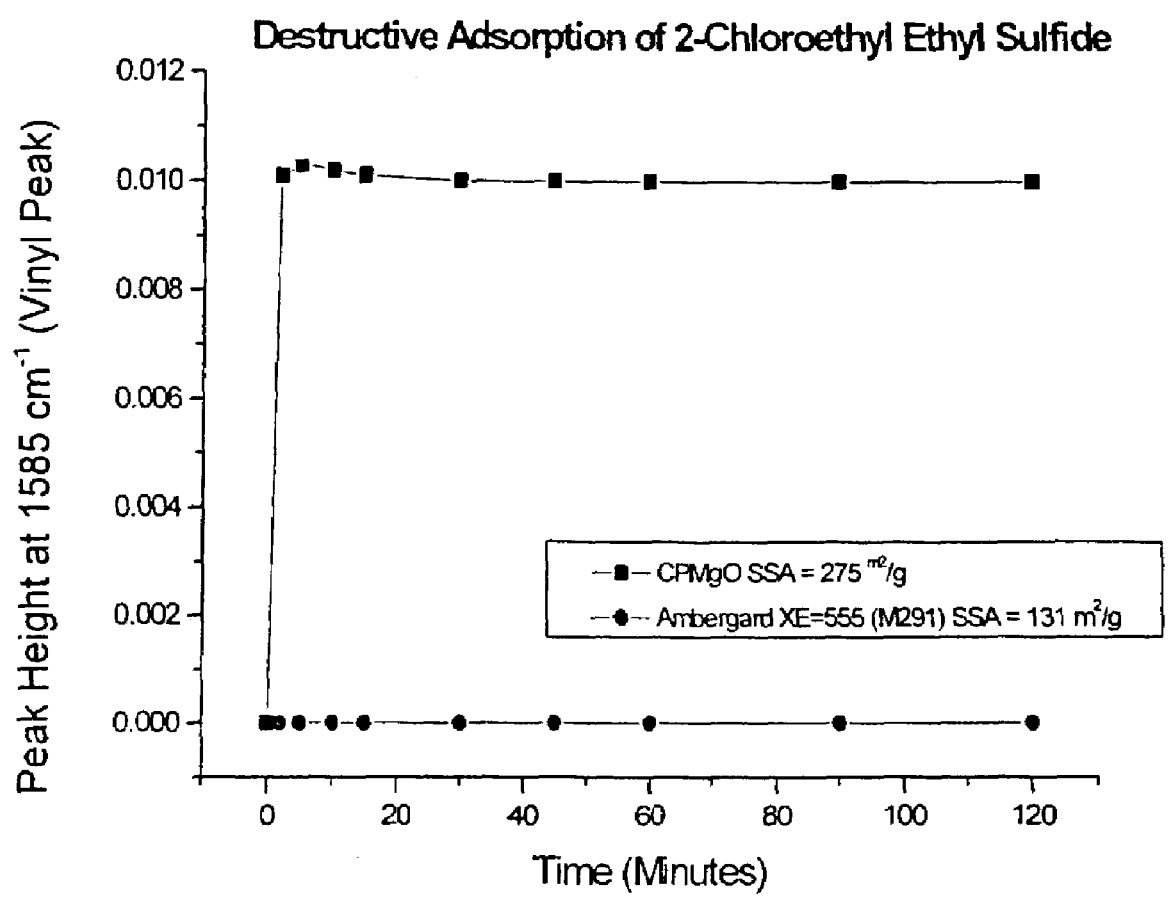
FIG. 5 is a graph illustrating the results of the comparative tests described in Example 5.

FIG. 5 graphically sets forth the results of this test demonstrating that the CP—MgO had a very significant destructive/chemisorptive effect, whereas the resin had no effect.

The metal oxides tested in Examples 1-5 were placed in a pressurized container as described above and allowed to sit at ambient temperature for about 2 weeks. Thereafter, metal oxide samples were taken from the containers and the above tests were repeated, without comparisons. The stored metal oxide powders gave virtually identical destructive/chemisorptive results against the CWS agents. This demonstrates that storing the oxides under pressure has no measurable deleterious effects on the performance thereof.

EXAMPLE 6

In this example, the effectiveness of destruction/chemisorption of 2-CEES was compared for different sorbent powder systems at two different sorbent:agent ratios. Three powder systems were employed: 100% MgO, 75% MgO/25% $TiO_2$, and 50% MgO/50% $TiO_2$. In the first set of trials, a quantity of 2-CEES was loaded onto a quantity of sorbent powder at a ratio of 10:1 (sorbent:agent) in a conical bottom, 4-dram vortex mixing vial. In the second set of trials, this ratio was lowered to 40:1 (sorbent:agent). Each mixture was capped and vortex mixed using a magnetic stirring plate for about 20 seconds. The destruction/chemisorption reaction was carried out at room temperature for 75 minutes. After this time, a quantity of extractive solvent (n-hexane) was added to each vial, followed by sonication for 20 minutes. Thereafter, each sample was centrifuged for 5 minutes to separate the pahses. A 5 ml aliquot of solvent was taken, and 5 μl of internal standard (n-decane) was added. The reaction products were then characterized using quantitative GC/MS. The results of these trials are noted below.

| Sample | Percent 2-CEES Removed | Percent 2-CEES Recovered | Sorbent/ Agent Ratio |
| --- | --- | --- | --- |
| 100% MgO | 10.2 ± 4.5 | 89.8 ± 4.5 | 10:1 |
| 75% MgO/25% $TiO_2$ | 40.1 ± 7.1 | 59.9 ± 7.1 | 10:1 |
| 50% MgO/50% $TiO_2$ | 60.4 ± 0.9 | 39.6 ± 0.9 | 10:1 |
| 100% MgO | 54.9 ± 3.4 | 45.1 ± 3.5 | 40:1 |
| 75% MgO/25% $TiO_2$ | 89.0 ± 3.1 | 11.0 ± 3.1 | 40:1 |
| 50% MgO/50% $TiO_2$ | 99.9 ± 0.1 | 0.1 ± 0.1 | 40:1 |

The results indicate that the greater the amount of $TiO_2$, the more effective the powder system was in removing the mustard gas simulant, 2-CEES. Also, as expected, the higher the sorbent/agent ratio, the more effective the powder system was.

All patents and other references mentioned herein are expressly incorporated by reference herein.

We claim:
1. Apparatus for area decontamination, comprising:
a container;
a pressurized, sprayable mixture within said container and including a quantity of MgO and $TiO_2$ particles, and a propellant, the weight ratio of MgO to $TiO_2$ being between about 99:1 to 1:99, said particles being present as aggregates having an average diameter of between about 50 nm-2 microns; and
a spray nozzle coupled with said container and selectively operable for generating a spray of said particles from the nozzle.
2. The apparatus of claim 1, said weight ratio of MgO to $TiO_2$ being between about 80:20 to 20:80.
3. The apparatus of claim 2, said weight ratio of MgO to $TiO_2$ being between about 70:30 to 30:70.
4. The apparatus of claim 1, said container comprising a metal, pressurizable bottle.
5. The apparatus of claim 1, said propellant including a suspension agent for said particles.
6. The apparatus of claim 1, said mixture being pressurized within said container to a level of from about 29-600 psi.

7. The apparatus of claim 1, said propellant selected from the group consisting of $N_2$, the noble gases, carbon dioxide, air, volatile hydrocarbons, fluorocarbons, and mixtures thereof.

8. The apparatus of claim 1, said container being selected from the group consisting of 2½ pound and 5 pound pressurized bottles.

9. A method of at least partially decontaminating an area subjected to an undesirable agent or substance, comprising the steps of providing the decontamination apparatus of claim 1, and manipulating said spray nozzle to generate a spray of metal oxide from the nozzle.

10. A method of at least partially decontaminating an area subjected to an undesirable agent or substance comprising the steps of:

providing a container, a sprayable mixture within said container including a quantity of MgO and $TiO_2$ particles, the weight ratio of MgO to $TiO_2$ being between about 99:1 to 1:99, and a spray nozzle presenting an outlet coupled with said container and selectively operable for generating a spray of said particles from the nozzle outlet, said particles being present as aggregates having an average diameter of between about 50 nm-2 microns;

creating a pressure gradient between the interior of said container and said nozzle outlet enabling said mixture to flow from said container toward said nozzle; and manipulating said spray nozzle to generate a spray of metal oxide from the nozzle.

11. The method of claim 10, said pressure gradient creation step comprising increasing the pressure within said container.

\* \* \* \* \*